United States Patent
Sheridan et al.

(10) Patent No.: US 8,276,480 B2
(45) Date of Patent: Oct. 2, 2012

(54) TORQUE-ADJUSTING DRIVE MECHANISM FOR A PROPELLABLE DEVICE

(75) Inventors: Timothy P. Sheridan, Eagan, MN (US); John J. Allen, Mendota Heights, MN (US)

(73) Assignee: FUJIFILM Corporation, Tokyo (JP)

( * ) Notice: Subject to any disclaimer, the term of this patent is extended or adjusted under 35 U.S.C. 154(b) by 864 days.

(21) Appl. No.: 12/402,306

(22) Filed: Mar. 11, 2009

(65) Prior Publication Data
US 2009/0233747 A1    Sep. 17, 2009

Related U.S. Application Data

(60) Provisional application No. 61/068,984, filed on Mar. 11, 2008.

(51) Int. Cl.
F16H 37/06    (2006.01)

(52) U.S. Cl. .................................... 74/665 R; 74/665 G

(58) Field of Classification Search ............ 74/640, 74/665 R, 665 F, 665 G, 665 GA, 331
See application file for complete search history.

(56) References Cited

U.S. PATENT DOCUMENTS

| | | | |
|---|---|---|---|
| 3,797,445 A | 3/1974 | Zeimer | |
| 4,866,516 A | 9/1989 | Hibino et al. | |
| 5,085,302 A | 2/1992 | Kriesels | |
| 5,662,587 A | 9/1997 | Grundfest et al. | |
| 5,819,736 A | 10/1998 | Avny et al. | |
| 6,038,488 A | 3/2000 | Barnes et al. | |
| 6,149,581 A | 11/2000 | Klingenstein | |
| 6,171,316 B1 | 1/2001 | Kovac et al. | |
| 7,044,245 B2 | 5/2006 | Anhalt et al. | |
| 7,235,046 B2 | 6/2007 | Anhalt et al. | |
| 7,387,179 B2 | 6/2008 | Anhalt et al. | |
| 2001/0041874 A1 | 11/2001 | Reydel | |
| 2001/0049972 A1 | 12/2001 | Sentmanat | |
| 2005/0054934 A1 | 3/2005 | Furnish et al. | |
| 2005/0272976 A1 | 12/2005 | Tanaka et al. | |
| 2006/0270901 A1 | 11/2006 | Bern et al. | |
| 2008/0183033 A1 | 7/2008 | Bern et al. | |
| 2008/0202266 A1* | 8/2008 | Hendrickson et al. | 74/331 |

FOREIGN PATENT DOCUMENTS

| | | |
|---|---|---|
| DE | 1756759 | 4/1970 |
| FR | 2481915 | 5/1980 |
| WO | WO-2009/114137 A2 | 9/2009 |

OTHER PUBLICATIONS

"International Application Serial No. PCT/US2009/001539, International Search Report mailed Oct. 26, 2009", 4 pgs.
"International Application Serial No. PCT/US2009/001539, Written Opinion Oct. 26, 2009", 4 pgs.
Extended European Search Report issued on Apr. 7, 2011 in the corresponding European Patent Application No. 09721078.5.

* cited by examiner

*Primary Examiner* — Justin Holmes
(74) *Attorney, Agent, or Firm* — Sughrue Mion, PLLC

(57) ABSTRACT

A drive mechanism includes a drive assembly including a driven element, a first driveshaft, configured to be engaged with the drive assembly, the first driveshaft configured to rotate in a first direction and relate a first assembly torque to the drive assembly and a first drive torque to the driven element, and a torque adjusting mechanism operatively engaged with the drive assembly and configured to relate a second assembly torque, opposite in direction to the first assembly torque, to the drive assembly.

24 Claims, 5 Drawing Sheets

TORQUE-ADJUSTING DRIVE MECHANISM FOR A PROPELLABLE DEVICE

CROSS-REFERENCE TO RELATED APPLICATIONS

This non-provisional application claims the benefit of priority under 35 U.S.C. §119(e) to U.S. Provisional Application Ser. No. 61/068,984, filed on Mar. 11, 2008, the specification of which is hereby incorporated by reference in its entirety.

FIELD

This patent document relates generally to drive mechanisms, and more specifically, to torque-adjusting drive mechanisms for a propellable device.

BACKGROUND

Drive mechanisms can be used to drive various objects. For example, some endoscope systems utilize a self-propellable device which helps carry an endoscope or other load. These self-propelled devices can be driven by a driveshaft that rotates to turn one or more gears within a drive mechanism of the self-propellable device to drive the device. However, the rotation of the driveshaft can result in undesired external torque on the device.

BRIEF DESCRIPTION OF THE DRAWINGS

The drawing illustrates generally, by way of example, but not by way of limitation, at least one embodiment discussed in the present document.

DETAILED DESCRIPTION

Figure 1:
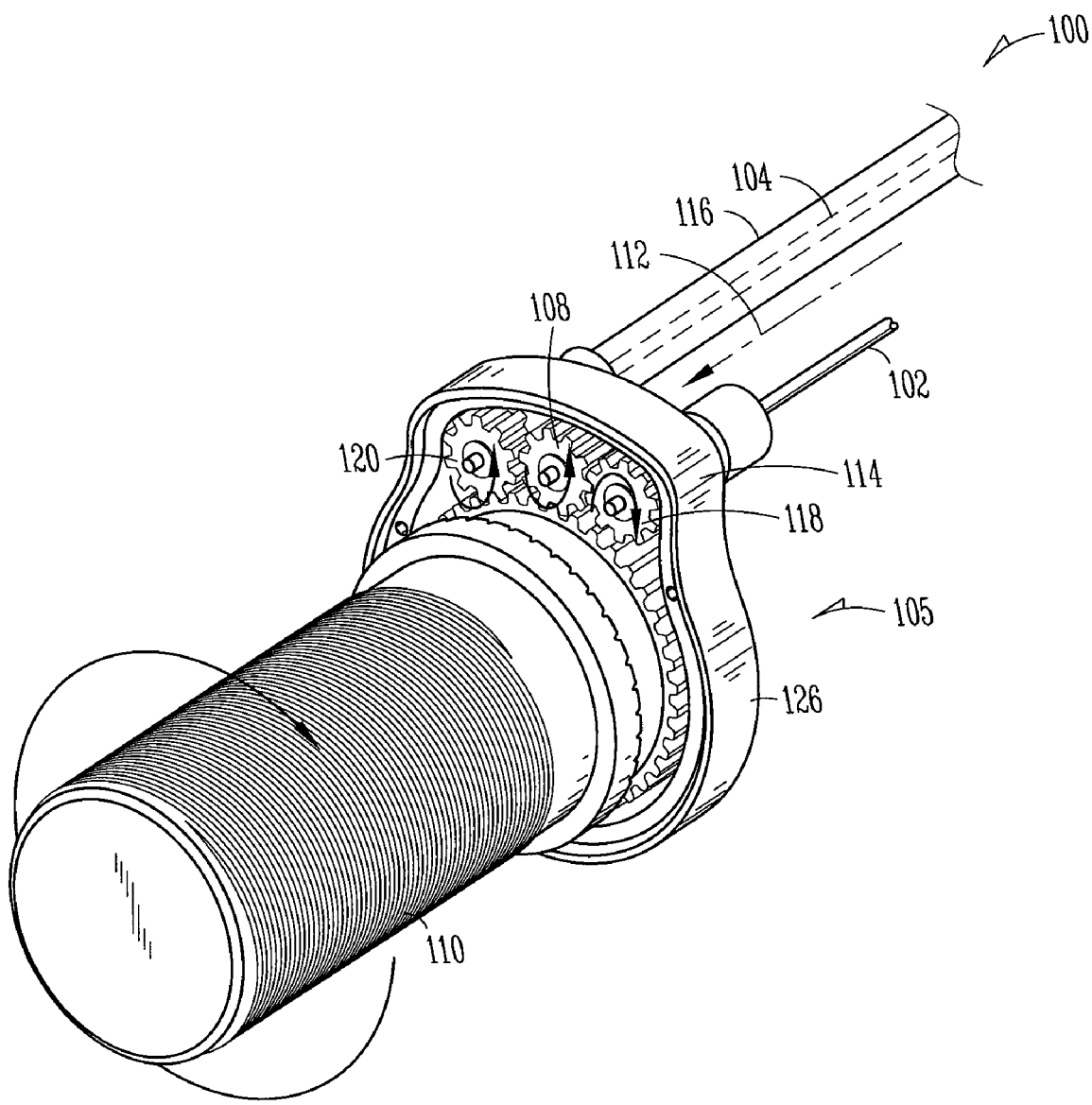
FIG. 1 illustrates an example of a schematic view of a torque-canceling or other torque-adjusting drive mechanism for use with a propellable device, the drive mechanism optionally configurable to result in a desired external device torque.

FIG. 1 illustrates an example of a torque-canceling or other torque-adjusting drive mechanism 100 for use by a propellable device, such as one or more of the propellable devices described in commonly-owned: U.S. Pat. No. 6,971,990, entitled "PROPULSION MECHANISM FOR ENDOCOPIC SYSTEMS," U.S. patent application Ser. No. 11/260,342 entitled "SELF-PROPELLABLE ENDOSCOPIC APPARATUS AND METHOD," and U.S. patent application Ser. No. 11/825,528 also entitled "SELF-PROPELLABLE ENDOSCOPIC APPARATUS AND METHOD," each of which is incorporated by reference herein in its entirety, including its disclosure of a propellable device.

In varying examples, the propellable devices described in the foregoing patent documents can include a permeable or impermeable self-enclosed tube, sized and shaped to fit within and engage a cavity, such as a human or animal body cavity. The tube can have an inner surface defining an enclosed region and an outer surface that is configured to turn outward to engage a wall of the cavity and turn inward to encompass a central region defining a concentric longitudinal path. The apparatus can further include an attachment coupled in proximity to the tube. The attachment can be configured to secure a load (e.g., an accessory) such as, for example, at a location at least partially in the central region. Upon securing of the load, the tube can be powered to provide movement relative to the cavity, thereby facilitating movement of the load with respect to the cavity in at least one of a forward or reverse direction generally along the longitudinal path.

In certain examples, such as shown in FIG. 1, the torque-canceling or torque-adjusting drive mechanism 100 configured for powering a tube of a propellable device can include two flexible, solid wire driveshafts 102, 104, such as for supplying mechanical power from an external location to the propellable device when the propellable device is located within a cavity, such as a human body cavity, for example. In some examples, the driveshafts 102, 104 can comprise one or more non-solid, flexible components also capable of delivering drive torque, such as wound cables, for example. Drive mechanism 100 also includes drive assembly 105 including a frame 126 and a driven element 110. Driveshafts 102, 104 are operatively coupled to drive assembly 105 to apply propulsive drive torque to driven element 110.

Figure 2:
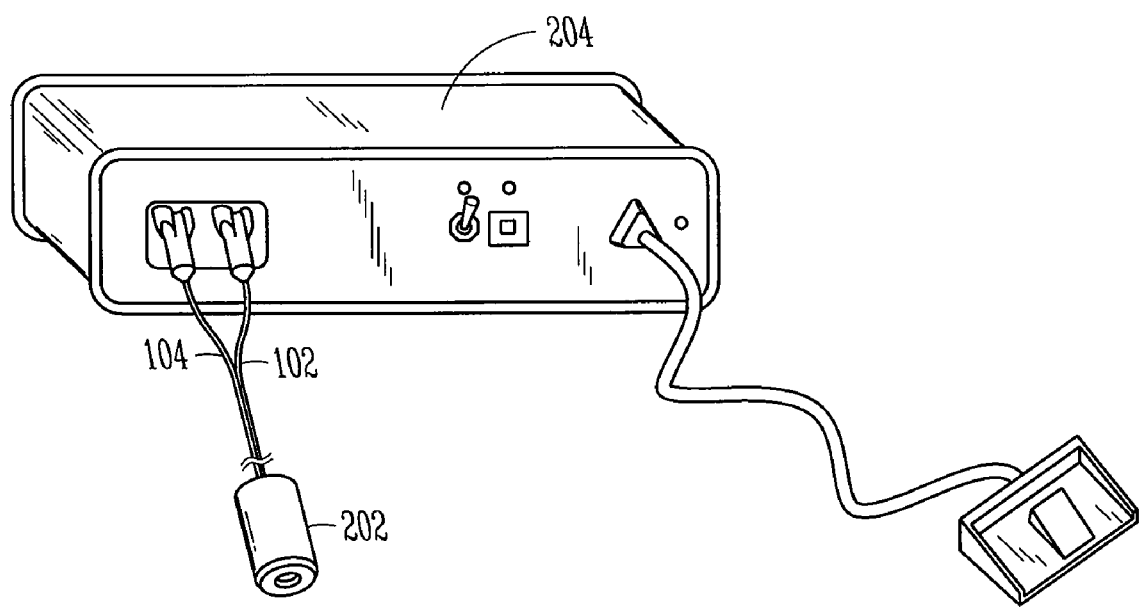
FIG. 2 illustrates an example of a propellable device connected to an electrical control unit.

FIG. 2 shows a propellable device 202, including the drive mechanism of FIG. 1, connected to an electrical control unit 204. The electrical control unit 204 can be coupled to the driveshafts 102, 104 and can be configured to apply an equal or approximately equal drive torque magnitude to each driveshaft, but to rotate them in opposite directions from each other. By having the driveshafts 102, 104 rotate in opposite directions, a resulting external tendency for the drive assembly 105 and the driven propellable device 202 to otherwise rotate about an axis 112 principally parallel to the axes of the driveshafts 102, 104 can be canceled, minimized or otherwise reduced. As a result, drive assembly 105, and the propellable device 202, as well as any load located within, or attached to, the propellable device 202 may not be subject to effects of the drive-based torque.

In the example shown, and referring again to FIG. 1, one of the driveshafts 102 or 104 is rotated in a first direction to relate a first drive torque to the driven element 110. At the same time, the driveshaft 102 or 104 relates a first assembly torque to the drive assembly 105. The other driveshaft 102 or 104 is rotated in a second direction, opposite the first direction which relates a second, opposite assembly torque to the drive assembly 105. The direction of rotation of the other driveshaft 102 or 104 can be reversed by an idler gear 108 (e.g., located at or near the propellable device) before its associated drive torque is applied to the driven element 110, which can take the form of, for example, a cylindrical worm gear configured to drive actuation of the propellable device. Accordingly, in this example, one of the drive shafts 102 or 104 and the idler gear 108 act as a torque adjusting mechanism configured to relate a second drive torque to the driven element 110 while applying a second, opposite assembly torque to drive assembly 105.

Consequently, both of the driveshafts 102, 104 can rotate in opposing directions at locations between the electrical control unit 204 and the propellable device 202, so as to apply a selected overall net assembly torque on drive assembly 105, yet can also both be used to apply unidirectional drive torque at the propellable device 202 to the driven element 110, such as for enhancing (e.g., doubling) the amount of mechanical power that can be delivered to the driven element 110 at any given rotational speed and associated drive torque. In certain examples, it is not necessary for the driveshafts 102, 104 to have the same rate of rotation. Instead, their applied drive torques can be made equal or substantially equal, so-as-to inhibit or prevent any noticeable net rotational effect of the propellable device 202, or the load located within or attached thereto, by the drive-based torques.

In some examples, it may be possible to have only one rotating driveshaft and to apply a drive-balancing, non-drive torque through a non-rotating element, such as a casing 116 surrounding the rotating driveshaft. For instance, the casing 116 can be attached to the machine frame 126, the driveshaft 102 can be omitted and the driveshaft 104 can be rotated in one direction to apply a single drive torque to the driven element 110 and a single assembly torque to the drive assembly 105. In this example, an opposing assembly torque can be applied to the casing 116 to negate or minimize any noticeable net rotation of the drive assembly 105 and the propellable device 202 caused by the drive torque. Thus, in this example, the casing 116 acts as a torque adjusting mechanism configured to relate a second torque, opposite in direction to the drive torque, to the drive assembly 105.

In some examples, the direction of rotation of one of the driveshafts 102, 104 can effectively be reversed, as received by the driven element 110, without the use of an idler gear 108.

Figure 3:
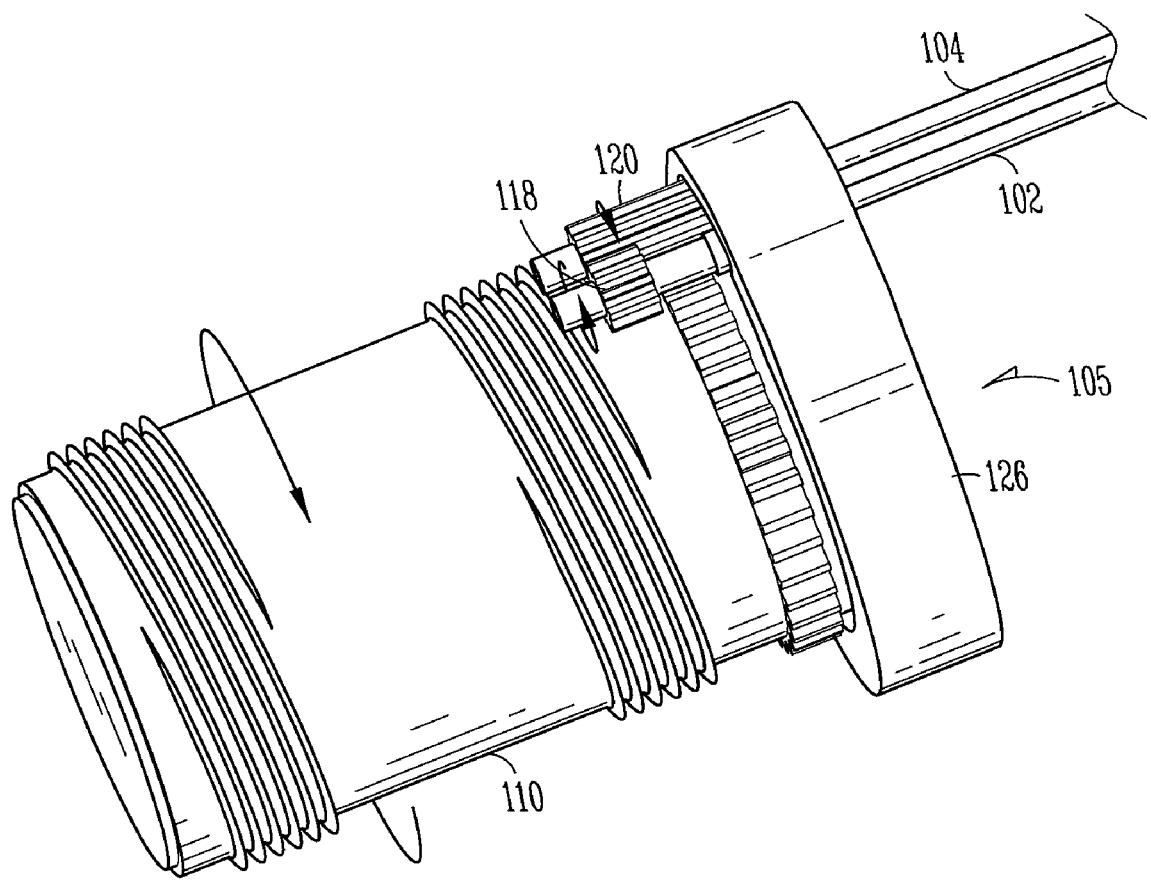
FIG. 3 illustrates a schematic view of an example of a second possible configuration of a torque-canceling or other torque-adjusting drive mechanism for use with a propellable device, the drive mechanism optionally configurable to result in a desired external device torque.

One such example is shown in FIG. 3. In this example, a first driven gear 118 coupled to a first driveshaft 102, which rotates in a first direction, can be engaged with a second driven gear 120 coupled with a second driveshaft 104, which rotates in a second direction opposite the first direction. Some distance away from the engagement between the first 118 and second 120 driven gears, a portion of either the first 118 or the second 120 driven gear can be engaged with a driven element 110 (e.g., a cylindrical worm gear).

Consequently, both of the driveshafts 102, 104 can rotate in opposing directions at locations between the electrical control unit 204 (see FIG. 2) and the engagement between the first 118 and second 120 driven gears, yet can both be used to apply unidirectional drive torque to the driven element 110, and thus to the propellable device 202, such as for enhancing (e.g., doubling) the amount of mechanical power that can be delivered to the driven element 110 at any given rotational speed and associated drive torque.

In certain examples, again referring to FIG. 1, a net external device torque resulting from the rotational torques of the first and second driveshafts 102, 104 on drive assembly 105, can be controlled in such a way as to not sum to zero or substantially zero, such that the driven propellable device 202 will rotate about an axis 112 principally parallel to the driveshafts 102, 104, as coupled to the driven element 110. The angle of rotation of the propellable device 202 can be controlled using the vector sum of the resulting external device torque divided by the torsional stiffness of the driveshaft casing assembly 114, the connective structure of the propellable device 202 to the load, or a sum of the two. This controlled angle of rotation can be utilized to steer the propellable device 202 through a cavity.

The driveshaft casing assembly 114 can be used to connect the propellable device 202, including the driven element 110, to the drive torque producing electrical control unit 204, such as via the draftshaft casings 116 and the driveshafts 102, 104. This technique can provide controlled orientation of the drive assembly 105 (and, therefore, the propellable device 202) if the electrical control unit 204 is controlled by a control system that is configured to controllably adjust the rotational torques of the driveshafts to provide or help provide the desired orientation.

Figure 4:
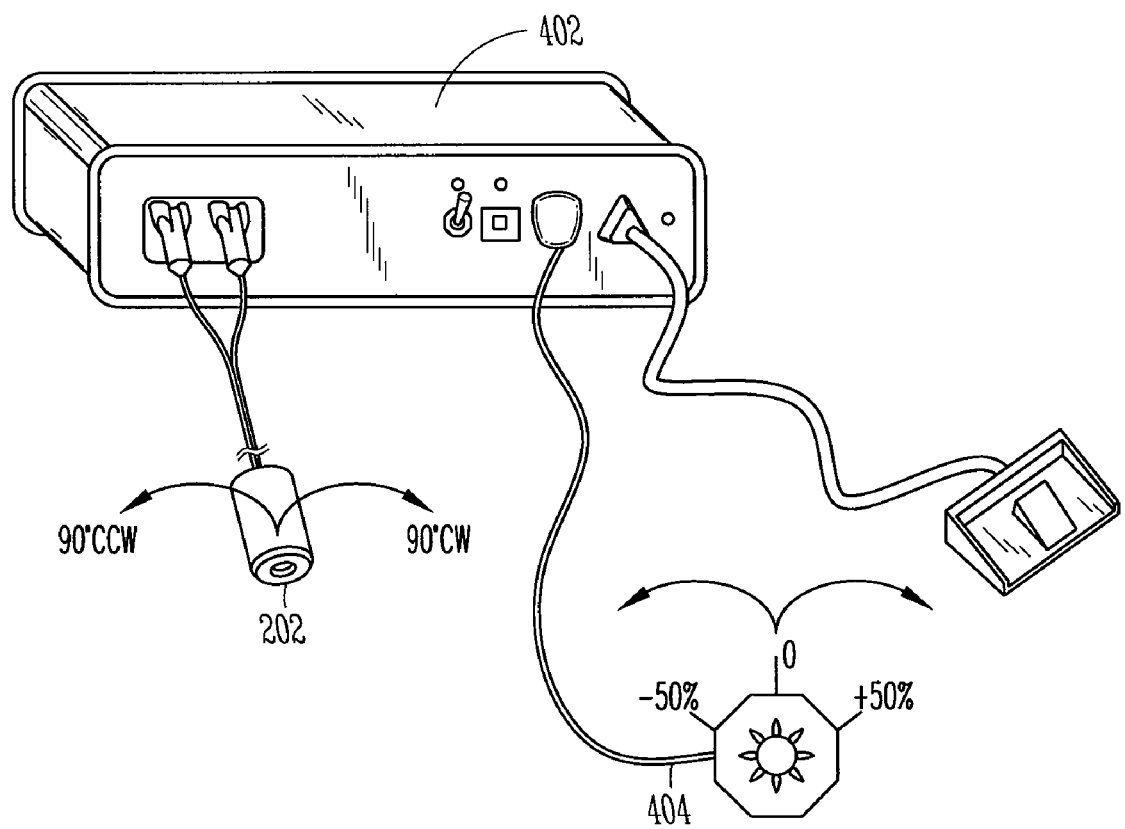
FIG. 4 illustrates an example of a propellable device attached to an electrical control unit, the control unit including a separate element for controlling one or more drive torques transmitted to the device.

FIG. 4 illustrates an electrical control unit 402, including a rotational control input mechanism 404, which allows the operator to deliver an electrical input to motor control circuitry or software to indicate a desired rotation of the propellable device 202.

For example, again referring to FIG. 1, the electrical control unit 402 can be configured such that the first driven gear 118 applies drive torque provided by a first driveshaft 102 to the driven element 110 via the idler gear 108, thereby reversing the sign of the applied drive torque vector inside a machine frame 126 of the propellable device 202 so it matches the direction of the drive torque supplied by a second driveshaft 104 and its second driven gear 120. This doubles the drive torque applied to the driven element 110. The drive torques transmitted to the first driven gear 118 and the second driven gear 120 at a location that is outside the machine frame 126 can be equal in magnitude but opposite in direction, in certain examples. Accordingly, in such examples, no net external rotation of the frame 126, and thus the propellable device 202, results.

A user of the electrical control unit 402 can vary the torques transmitted by the driveshafts 102, 104 via the rotational control input mechanism 404. If the torques are provided such that they are not equal in magnitude, the drive assembly 105 and the propellable apparatus 202 will rotate about an axis 112 that is substantially parallel to the driveshaft axes, through an angle that can be determined as the resulting external machine frame 126 and propellable device 202 torque divided by the torsional stiffness of the driveshaft casing assembly 114.

Figure 5:
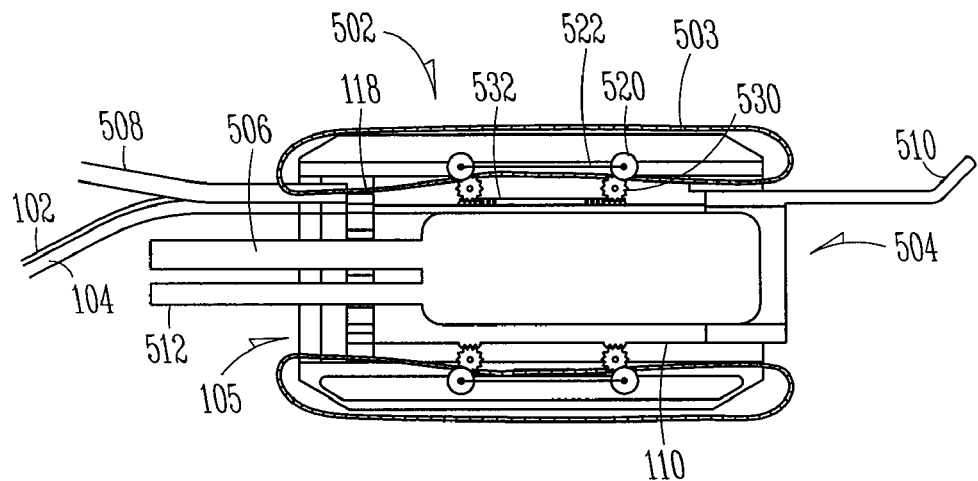
FIG. 5 illustrates an example of an embodiment of a propellable device that can be steered, in part, using an external device torque resulting from an imbalance of counter-rotating drive torques delivered to the device.

FIG. 5 illustrates one possible propellable device application where the electrical control mechanism 402 described in association with FIG. 4 may be beneficial. The example propellable device 502 shown in this example can be used as a means to advance one or both of diagnostic or therapeutic elements through body lumens, such as the colon or small intestine.

In this example, propellable device 502 includes a toroidal, self enclosed tube 503 that can be propelled by an assembly including a support structure 522 located within an enclosed region of the self-enclosed tube 503 and a drive structure 532 located within the central open area of the self-enclosed tube 503. Driven element 110 includes threads that engage and rotate wheels 530 of drive structure 532. Skids or wheels 520 located on support structure 522 are biased toward wheels 530 with the flexible material of the self-enclosed tube 503 pinched therebetween. The rotation of the wheels 530 thus rotates the flexible material and the propellable device 502 moves forward or backward as desired. As discussed above, the rotation of driveshafts 102, 104 provide drive torque to gears 118, 108, 120 (see FIG. 1) which in turn provide drive torque to driven element 110.

As shown, the propellable device 502 can be mounted over a module 504 containing a forward looking camera and light elements. Connected to the back of the module 504 can be a flexible electrical bundle 506 containing wires to operate the camera and light elements and a working channel 512. Additionally, there can be a flexible tube 508, which passes through the module 504 so that other devices can be passed through the tube 508 from a first end located outside the body cavity to and through an opening at the tip of the module 504. A curved tip element 510 can also be attached to the module 504 at its tip. This curved tip element 510 can act to steer the device 502, as the tip can be torqued to different orientations using the differential drive torque method described above via the driveshafts 102, 104 to drive assembly 105 and propellable device 502. In this way, the curved tip element 510 can be steered to align with a desired path in the body cavity as the device is advanced into and through such cavity.

Although FIG. 1 illustrates an example that can be used as a torque-canceling or torque-adjusting drive mechanism 100 including two driveshafts 102, 104, the present subject matter is not so limited. For example, a number of driveshafts greater than two can also be used, for example, such that the vector sum (magnitude and direction) of the external torques applied to drive assembly 105, resulting from the drive torques, is substantially equal to zero, in certain examples. If such external torques outside the drive assembly 105 sum to substantially zero, there is substantially no net torque (and therefore substantially no net rotation) of the driven propellable device 202. The plurality of driveshafts can be configured to rotate in alternating directions, rotate in a second direction opposite to that of a first driveshaft, and/or rotate in the same direction as the first driveshaft. It is believed that additional driveshafts (e.g., beyond two) can help, in certain examples, to (1) deliver more power to the driven element 110; (2) allow for the use of smaller diameter, more flexible driveshafts for a given power lever; or (3) allow for multiple functions (e.g., motion and cutting) to be executed concurrently or simultaneously.

Figure 6:
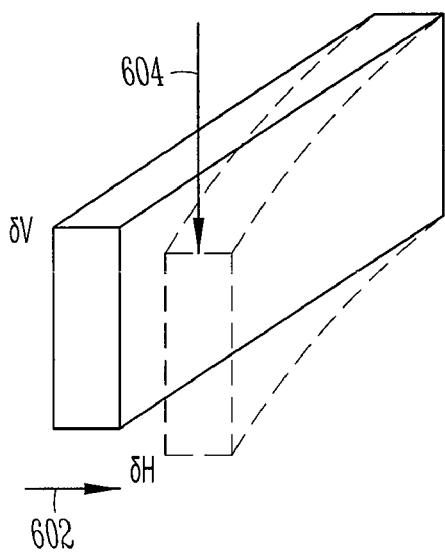
FIG. 6 illustrates an example of a structure exhibiting lateral deflection when subjected to a bending stress.
Figure 7:
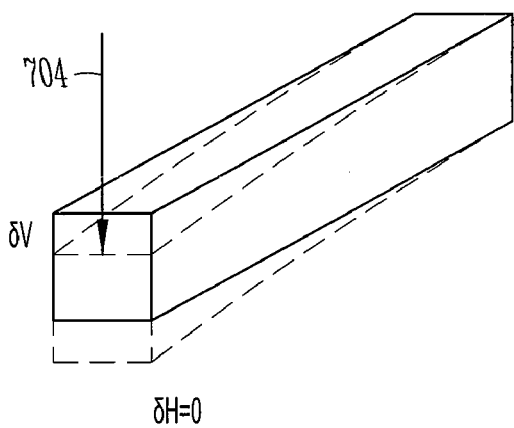
FIG. 7 illustrates an example of a structure exhibiting little to no lateral deflection when subjected to a bending stress.

The flexible driveshafts 102, 104 will invariably be subject to bending as they traverse one or more cavity corners, such as one or more human or animal cavity corners. This bending may lead to lateral deflection of the driveshafts 102, 104, which can potential cause discomfort or even injury to a human or animal, or damage to another cavity-bearing structure. For at least this reason, it may be beneficial to eliminate or at least minimize the lateral deflection that results when the driveshafts 102, 104 bend around the cavity or other corners. In various examples, it has been found that lateral driveshaft deflection can be eliminated or at least minimized by distributing placement of the drive mechanism 100 components to equalize the cross-sectional mechanism stiffness in the planar principal axes. When the stiffness in the planar principal axes is not equal, a structure can exhibit a lateral deflection 602 when subject to a bending force 604, as shown in FIG. 6. In contrast, when the stiffness in the planar principal axes is equal or substantially equal, a structure may exhibit little to no lateral deflection when subject to a bending force 704, as shown in FIG. 7.

When considering the construction of drive mechanisms 100 including two or more driveshafts 102, 104, where the components of the drive mechanism have differing physical properties, careful consideration of how to distribute the components such that a mechanism cross-sectional stiffness in the principal axes is equal or substantially equal can be made. Due, at least in part, to the differing physical properties, it is likely that geometric cross-section symmetry of the drive mechanism 100 will not necessarily lead to equal cross-sectional stiffness. In some examples, drive mechanism 100 component distributions having equal or substantially equal cross-section stiffness in the principal axes can be found using elasticity theory iterative techniques. In some examples, drive mechanism 100 component distributions having equal or substantially equal cross-section stiffness in the principal axes can be found with the help of modern 3D Computer-Aided design (CAD) systems.

Additional Notes

The above Detailed Description includes references to the accompanying drawings, which form a part of the Detailed Description. The drawings show, by way of illustration, specific embodiments in which the invention can be practiced. These embodiments are also referred to herein as "examples." Such examples can include elements in addition to those shown and described. However, the present inventor also contemplates examples in which only those elements shown and described are provided.

All publications, patents, and other patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A drive mechanism comprising:
   a drive assembly including a driven element;
   a first driveshaft, configured to be engaged with the drive assembly, the first driveshaft configured to rotate in a first direction and relate a first assembly torque to the drive assembly and a first drive torque to the driven element; and
   a torque adjusting mechanism operatively engaged with the drive assembly and configured to relate a second assembly torque, opposite in direction to the first assembly torque, to the drive assembly,
   wherein the torque adjusting mechanism includes a second driveshaft, configured to rotate in a second direction that is opposite to the first direction and relate the second assembly torque to the drive assembly and relate a second drive torque to the driven element, and
   both the first assembly torque of the first driveshaft and the second assembly torque of the second driveshaft are applied to the driven element.

2. The drive mechanism of claim 1, wherein one of the first direction or the second direction is reversed its direction and the other one of the first direction or the second direction is maintained its direction,
   the first drive torque and the second drive torque are applied to the one driven element.

3. The drive mechanism of claim 1 or claim 2, wherein the torque adjusting mechanism includes an idler gear, configured to be coupled with the driven element, the idler gear configured to communicate with one of the first driveshaft or the second driveshaft to reverse a rotational direction of the drive torque thereby provided for relating to the driven element a unidirectional drive torque.

4. The drive mechanism of claim 3, wherein an amount of power related to the driven element is enhanced through the unidirectional application of drive torque from the first and second driveshafts, as compared to a relating of drive torque from only one of the first and second driveshafts.

5. The drive mechanism of claim 3, wherein the first driveshaft and second driveshaft each have a driveshaft casing at least partially surrounding the respective driveshaft, and
   wherein the driveshafts and their respective casings are configured in combination to yield a substantially equal bending stiffness when bending in one or more axes divergent from the longitudinal axes of the driveshafts.

6. The drive mechanism of claim 1 or claim 2,
   wherein a portion of one of the first driveshaft or the second driveshaft is engaged with the driven element to unidirectionally relate the first and second drive torques thereto, and
   wherein one of the first or second drive torque is applied to the driven element throughout the other one of the first or second drive shaft.

7. The drive mechanism of claim 6, wherein an amount of power related to the driven element is enhanced through the unidirectional relating of the first and second drive torques from the first and second driveshafts, as compared to a relating of only one of the first drive torque or the second drive torque.

8. The drive mechanism of claim 6, wherein the first driveshaft and second driveshaft each have a driveshaft casing at least partially surrounding the respective driveshaft, and
   wherein the driveshafts and their respective casings are configured in combination to yield a substantially equal bending stiffness when bending in one or more axes divergent from the longitudinal axes of the driveshafts.

9. The drive mechanism of claim 1, wherein an axis of the driven element, an axis of the first driveshaft and an axis of the second driveshaft are parallel each other.

10. The drive mechanism of claim 1, wherein the torque adjusting mechanism includes a casing at least partially surrounding the first driveshaft and attached to a frame of the drive assembly, wherein the casing is configured to be non-rotating relative to the first driveshaft such that the second assembly torque includes a non-drive torque applied by the casing to the drive assembly.

11. The drive mechanism of claim 1, wherein the torque adjusting mechanism includes a plurality of driveshafts, the plurality of driveshafts being configured to be engaged with the drive assembly.

12. A system comprising:
    a propellable device; and
    a drive mechanism configured to provide at least one of a forward or backward advancement of the propellable device, the drive mechanism including,
    a drive assembly including a driven element;
    a first driveshaft, configured to be engaged with the drive assembly, the first driveshaft configured to rotate in a first direction and relate a first assembly torque to the drive assembly and a first drive torque to the driven element; and
    a torque adjusting mechanism operatively engaged with the drive assembly and configured to relate a second assembly torque, opposite in direction to the first assembly torque, to the drive assembly,
    wherein the torque adjusting mechanism includes a second driveshaft, configured to rotate in a second direction that is opposite to the first direction and relate the second assembly torque to the drive assembly and relate a second drive torque to the driven element, and
    both the first assembly torque of the first driveshaft and the second assembly torque of the second driveshaft are applied to the driven element.

13. The system of claim 12, wherein the torque adjusting mechanism includes an idler gear, configured to be coupled with the driven element, the idler gear configured to communicate with one of the first driveshaft or the second driveshaft to reverse a rotational direction of the drive torque thereby provided for relating to the driven element a unidirectional drive torque.

14. The system of claim 13, further including an electrical control unit coupled to the first and second driveshafts and configured to apply an equal or approximately equal torque magnitude to each driveshaft.

15. The system of claim 13, further including an electrical control unit with a rotational control input mechanism to deliver an input to a motor control circuitry or software, the input including instructions to concurrently control a desired propulsive drive torque magnitude, including a net of the first and second drive torques, and a desired rotation of the propellable device, including a net of the first and second assembly torques.

16. The system of claim 12, wherein the torque adjusting mechanism includes a second driveshaft, configured to rotate in a second direction that is opposite to the first direction and relate the second assembly torque to the drive assembly and relate a second drive torque to the driven element, and
wherein a portion of one of the first driveshaft or the second driveshaft spaced from the engagement between the first and second driveshafts is engaged with the driven element to unidirectionally relate the first and second drive torques thereto.

17. The system of claim 16, further including an electrical control unit coupled to the first and second driveshafts and configured to apply an equal or approximately equal torque magnitude to each driveshaft.

18. The system of claim 16, further including an electrical control unit with a rotational control input mechanism to deliver an input to a motor control circuitry or software, the input including instructions to concurrently control a desired propulsive drive torque magnitude, including a net of the first and second drive torques, and a desired rotation of the propellable device, including a net of the first and second assembly torques.

19. The system of claim 12, wherein the torque adjusting mechanism includes a casing at least partially surrounding the first driveshaft and attached to a frame of the drive assembly, wherein the casing is configured to be non-rotating relative to the first driveshaft such that the second assembly torque includes a non-drive torque applied by the casing to the drive assembly.

20. A method comprising:
rotating a first driveshaft in a first direction and thereby applying a first drive torque to a driven element of a drive assembly and a first assembly torque to the drive assembly; and
applying a second, directionally-opposite, assembly torque by a torque adjusting mechanism operatively engaged with the drive assembly and configured to relate the second assembly torque to the drive assembly,
wherein applying the second, directionally-opposite, assembly torque by the torque adjusting mechanism includes using a second driveshaft, configured to rotate in a second direction that is opposite to the first direction and relate the second assembly torque to the drive assembly and relate a second drive torque to the driven element,
both the first assembly torque of the first driveshaft and the second assembly torque of the second driveshaft are applied to the driven element.

21. The method of claim 20, wherein applying the second, directionally-opposite, assembly torque by the torque adjusting mechanism includes using an idler gear, configured to be coupled with the driven element, the idler gear configured to communicate with one of the first driveshaft or the second driveshaft to reverse a rotational direction of the drive torque thereby provided for relating to the driven element a unidirectional drive torque.

22. The method of claim 20,
wherein a portion of one of the first driveshaft or the second driveshaft spaced from the engagement between the first and second driveshafts is engaged with the driven element to unidirectionally relate the first and second drive torques thereto.

23. The method of claim 20, wherein applying the second, directionally-opposite, assembly torque by the torque adjusting mechanism includes using a casing at least partially surrounding the first driveshaft and attached to a frame of the drive assembly, wherein the casing is configured to be non-rotating relative to the first driveshaft such that the second assembly torque includes a non-drive torque applied by the casing to the drive assembly.

24. The method of claim 20, wherein the torque adjusting mechanism is used to control an external rotational assembly torque imparted to the drive assembly by the first and second assembly torques, such that an external rotational torque delivered to the drive assembly is used to at least partially control a position of the drive assembly.

\* \* \* \* \*